United States Patent [19]

Staniforth

[11] Patent Number: 5,004,614

[45] Date of Patent: Apr. 2, 1991

[54] CONTROLLED RELEASE DEVICE WITH AN IMPERMEABLE COATING HAVING AN ORIFICE FOR RELEASE OF DRUG

[75] Inventor: John N. Staniforth, Bath, England

[73] Assignee: Forum Chemicals Ltd., Redhill, England

[21] Appl. No.: 398,632

[22] Filed: Aug. 25, 1989

[51] Int. Cl.$^5$ ............................................. A61K 9/22
[52] U.S. Cl. ................................. 424/466; 424/473; 424/78; 424/79; 424/482; 424/483
[58] Field of Search ............... 424/472, 473, 466, 471, 424/467

[56] References Cited

U.S. PATENT DOCUMENTS

| | | | |
|---|---|---|---|
| 3,146,169 | 8/1964 | Stephenson et al. | 424/467 |
| 3,845,770 | 11/1974 | Theeuwes et al. | 424/15 |
| 3,924,622 | 12/1975 | Brooke | 128/260 |
| 3,952,741 | 4/1976 | Baker | 128/260 |
| 4,014,884 | 3/1977 | Theeuwes et al. | 128/260 |
| 4,036,227 | 7/1977 | Zaffaroni et al. | 128/260 |
| 4,058,122 | 11/1977 | Theeuwes et al. | 128/260 |
| 4,077,407 | 3/1978 | Theeuwes et al. | 128/260 |
| 4,096,238 | 6/1978 | Zaffaroni et al. | 424/15 |
| 4,111,203 | 9/1978 | Theeuwes | 128/260 |
| 4,116,241 | 9/1978 | Theeuwes et al. | 128/260 |
| 4,160,020 | 7/1979 | Ayer et al. | 424/15 |
| 4,160,452 | 7/1979 | Theeuwes | 128/260 |
| 4,218,433 | 8/1980 | Kooichi et al. | 424/15 |
| 4,235,236 | 11/1980 | Theeuwes | 128/260 |
| 4,271,113 | 6/1981 | Luschen | 264/112 |
| 4,449,983 | 5/1984 | Cortese et al. | 424/473 |
| 4,519,801 | 5/1985 | Edgren | 604/892 |
| 4,601,893 | 7/1986 | Cardinal | 424/15 |
| 4,609,374 | 9/1986 | Ayer | 424/19 |
| 4,610,686 | 9/1986 | Ayer et al. | 604/890 |
| 4,612,008 | 9/1986 | Wong et al. | 604/892 |
| 4,624,847 | 11/1986 | Ayer et al. | 424/15 |
| 4,687,660 | 8/1987 | Baker et al. | 424/465 |
| 4,693,886 | 9/1987 | Ayer | 424/15 |
| 4,772,474 | 9/1988 | Eckenhoff et al. | 424/465 |
| 4,792,448 | 12/1988 | Ranade | 424/438 |
| 4,803,076 | 2/1989 | Randae | 424/438 |
| 4,814,182 | 3/1989 | Graham et al. | 424/484 |
| 4,814,183 | 3/1989 | Zentner | 424/485 |
| 4,816,262 | 3/1989 | McMullen | 424/467 |
| 4,830,860 | 5/1989 | Ranade | 424/486 |
| 4,857,330 | 8/1989 | Stephens et al. | 424/471 |

OTHER PUBLICATIONS

"Zero-Order Controlled Release Polymer, Matrices for Micro- and Macromolecules", D. Hsieh et al., J. Pharm. Sciences, vol. 72, No. 1, 1/83.

"A New Ibuprofen Pulsed Release Oral Dosage Form", U. Conte et al., presented at the 8th Pharmaceutical Technology Conference, 3/29/89, vol. 1.

Primary Examiner—Thurman K. Page
Assistant Examiner—James M. Spear
Attorney, Agent, or Firm—Kenyon & Kenyon

[57] ABSTRACT

Controlled release devices having a core including an active agent and an outer coating which is substantially impermeable to the entrance of an environmental fluid and substantially impermeable to the release of the active agent during a dispensing period allow the controlled release of the active agent through an orifice in the outer coating.

27 Claims, 12 Drawing Sheets

FIG. 1
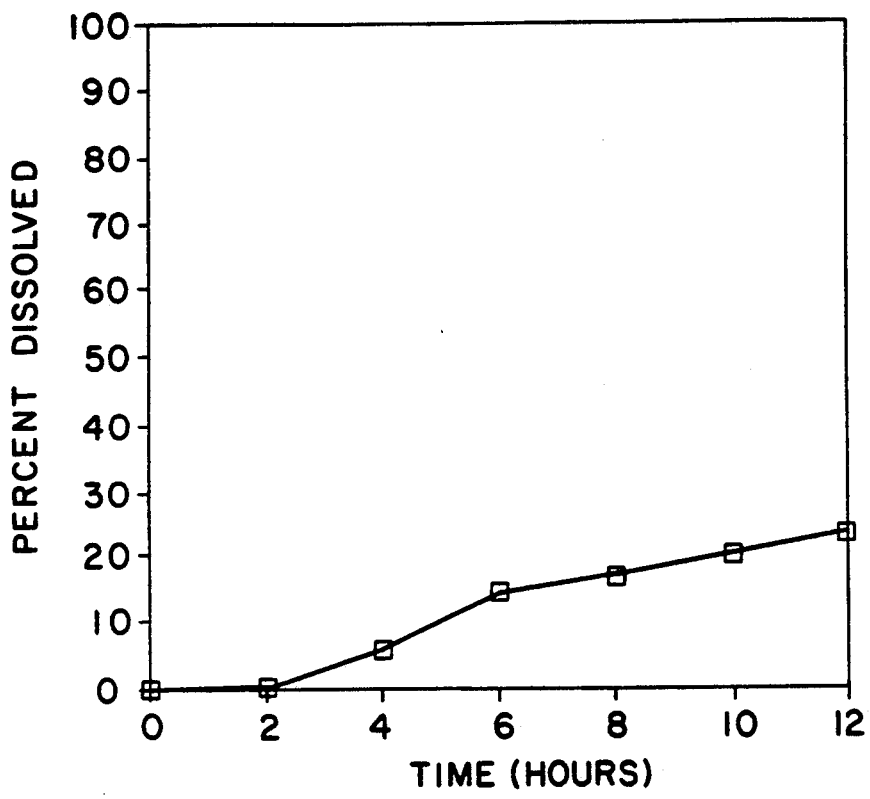
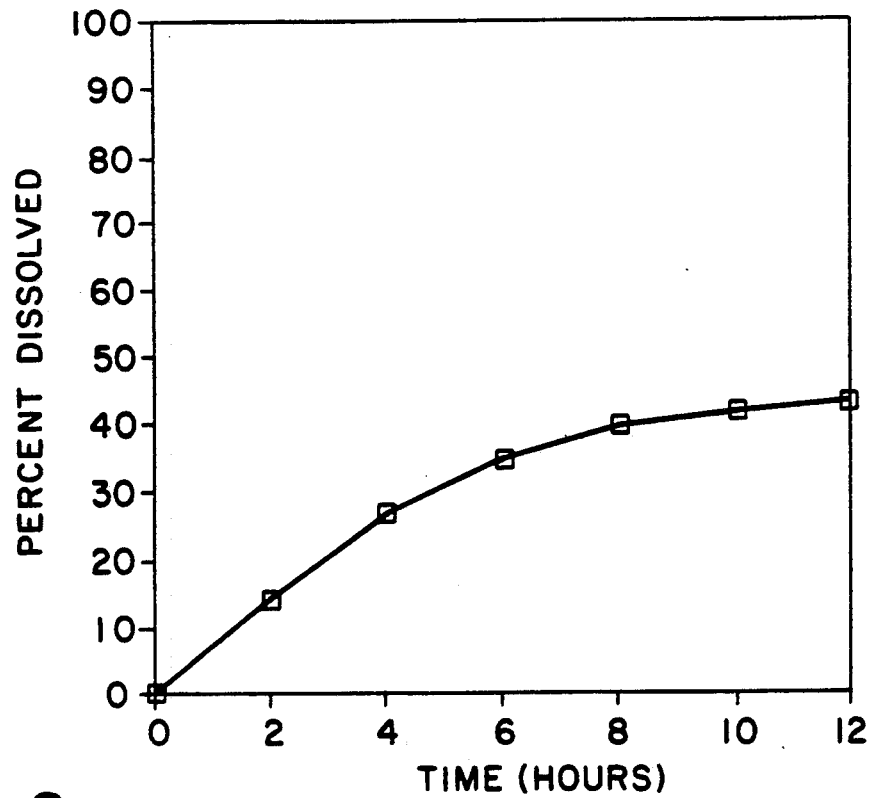
FIG. 2

FIG. 3
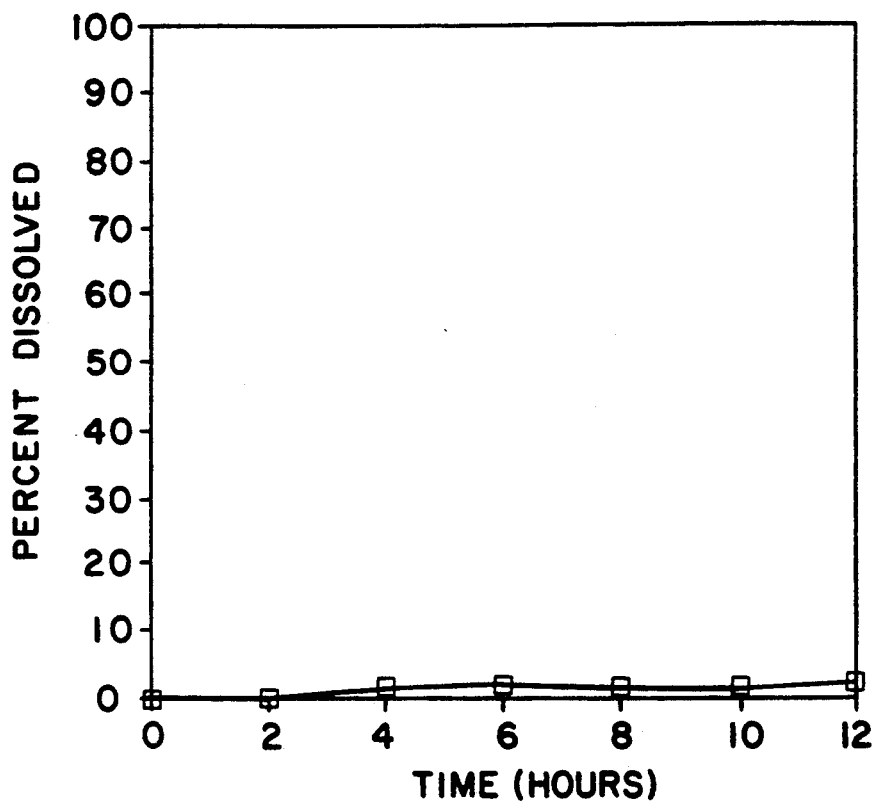
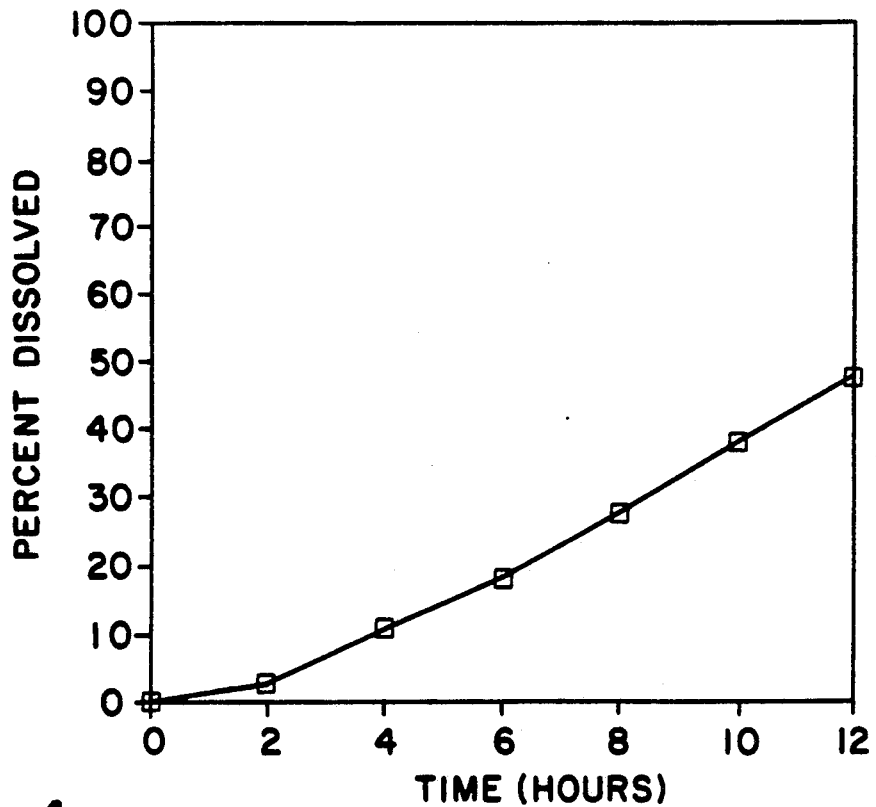
FIG. 4

FIG. 5
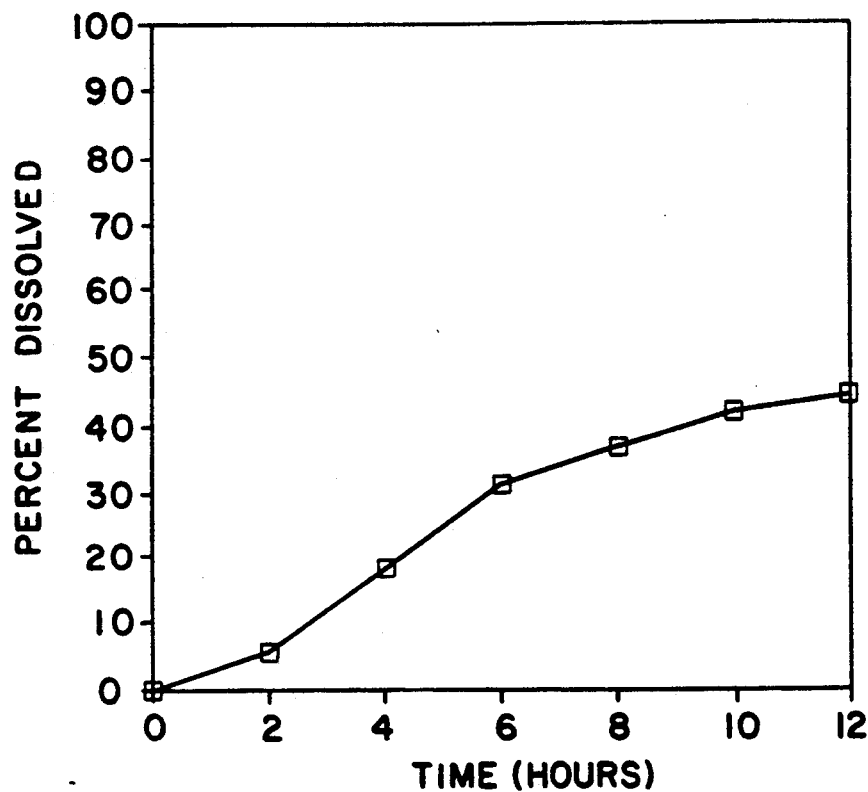
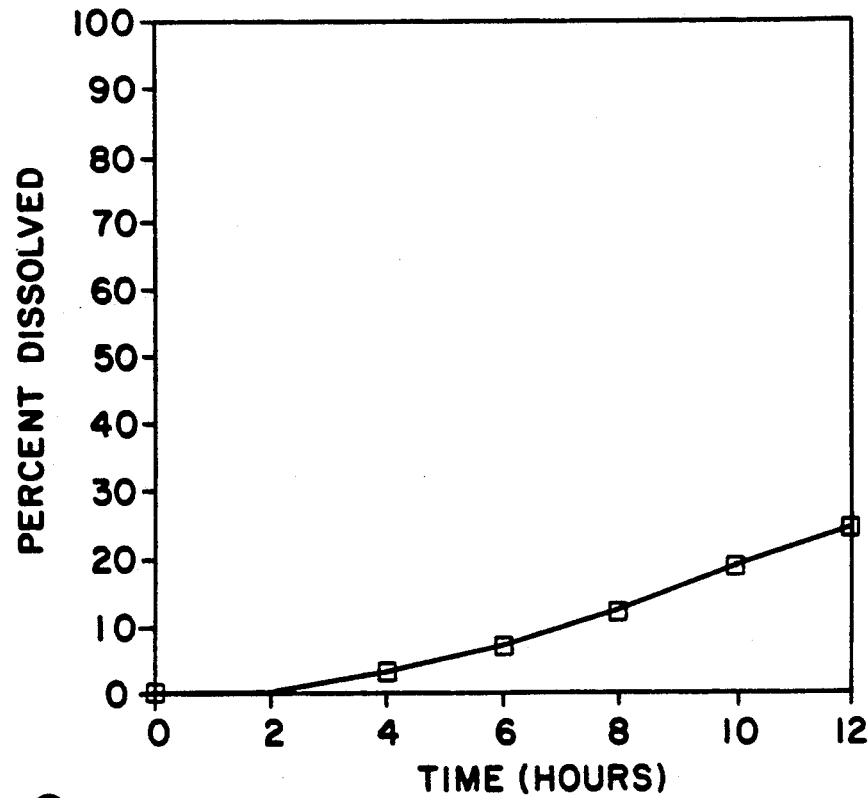
FIG. 6

FIG. 7
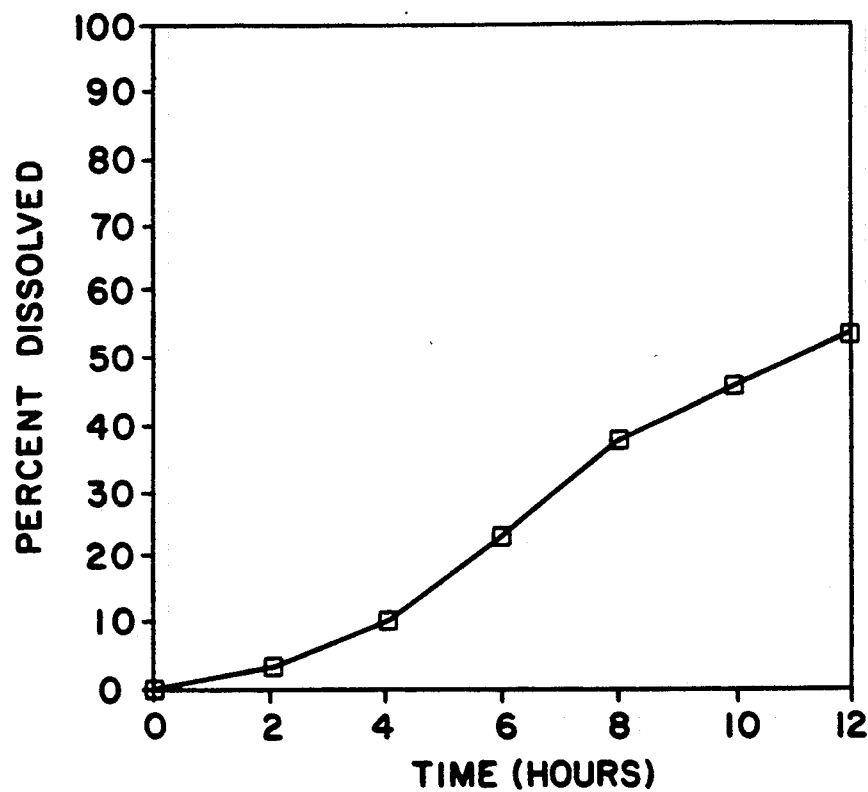
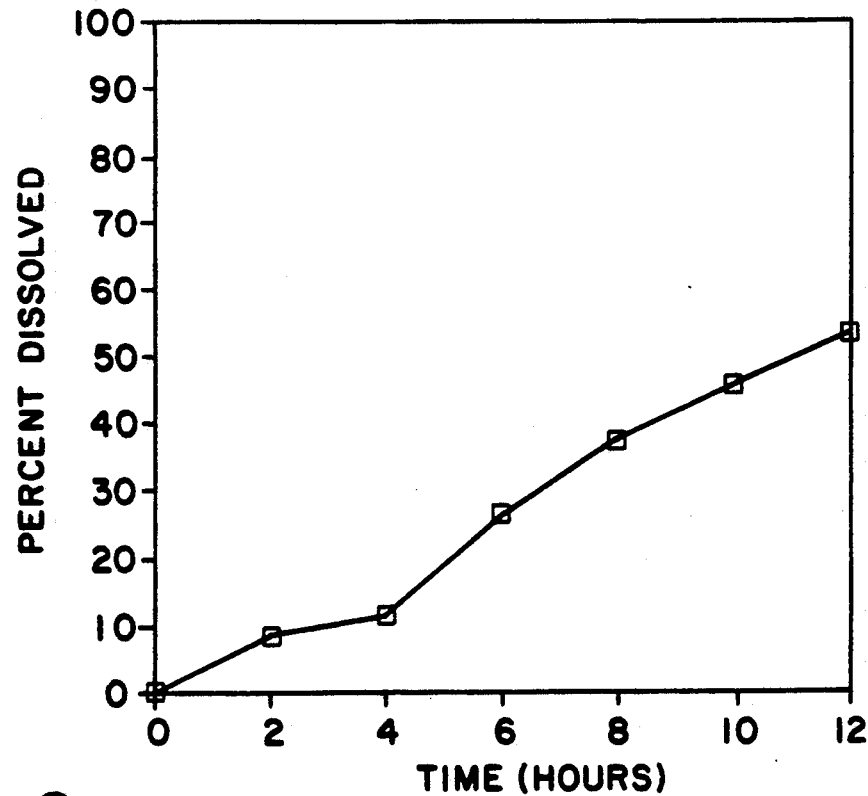
FIG. 8

FIG. 9
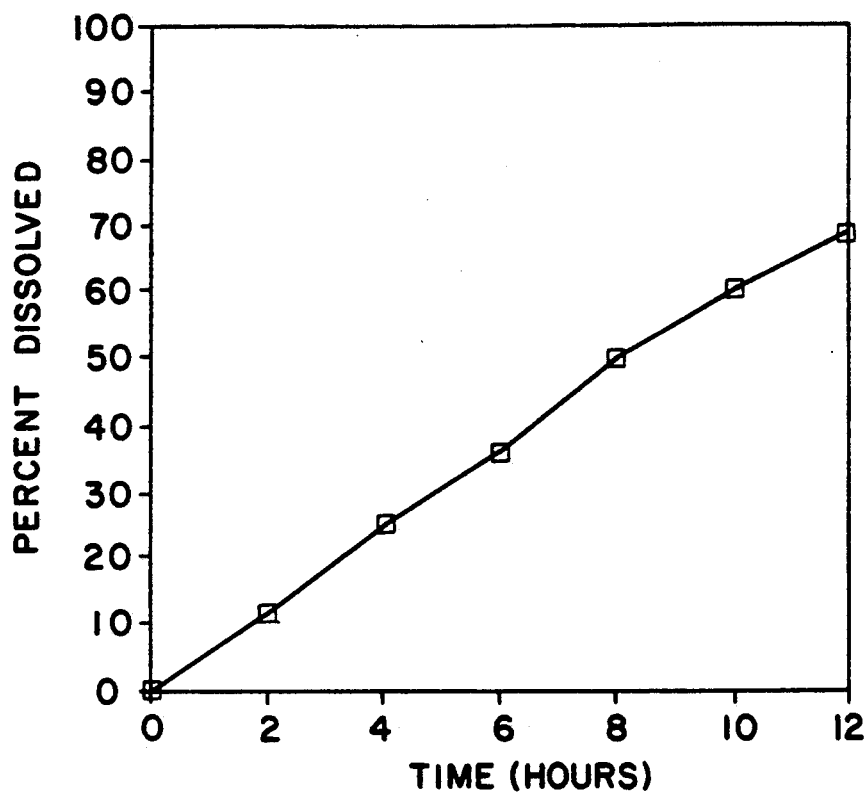
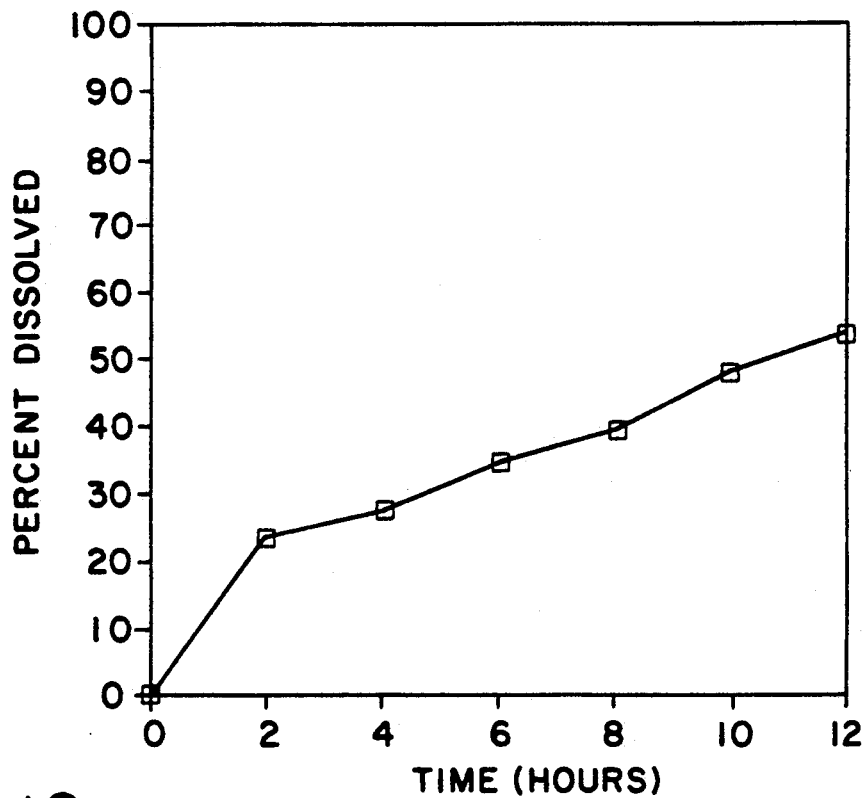
FIG. 10

FIG. 11
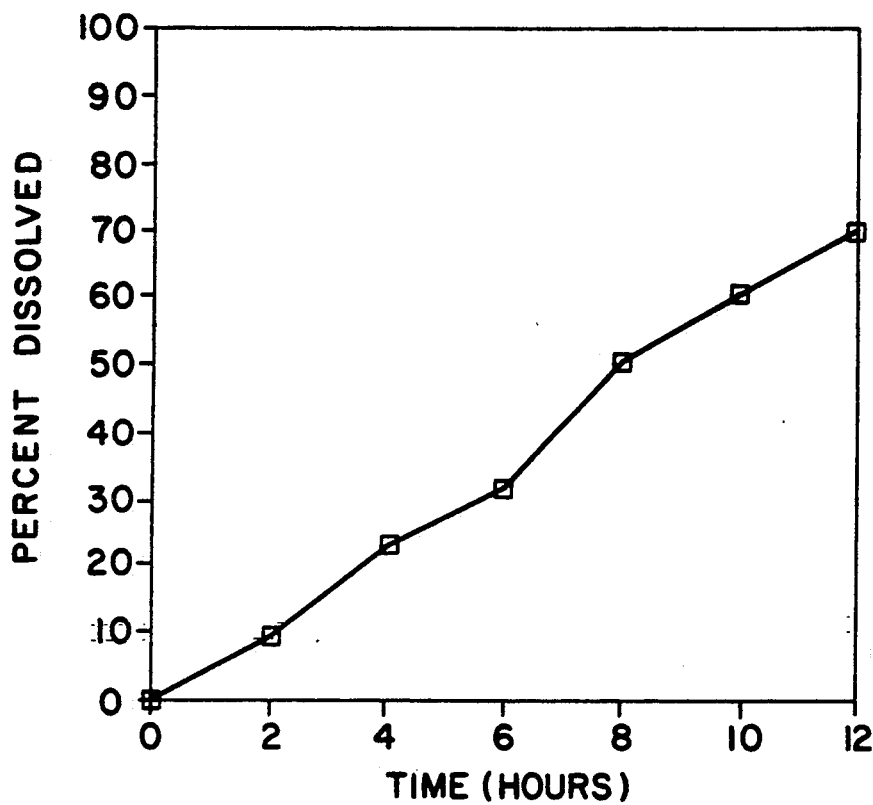
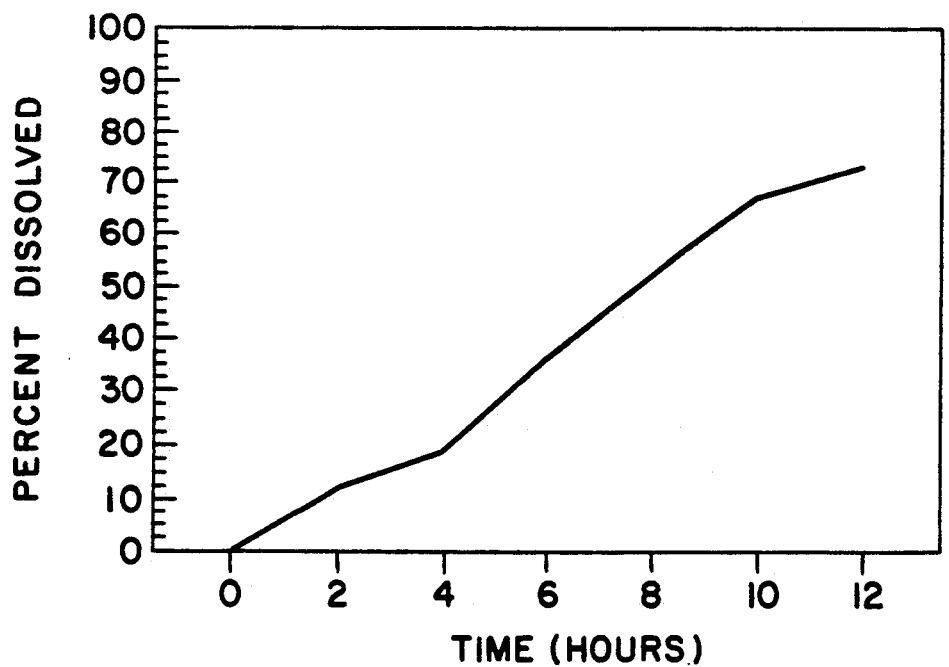
FIG. 12

FIG. 13
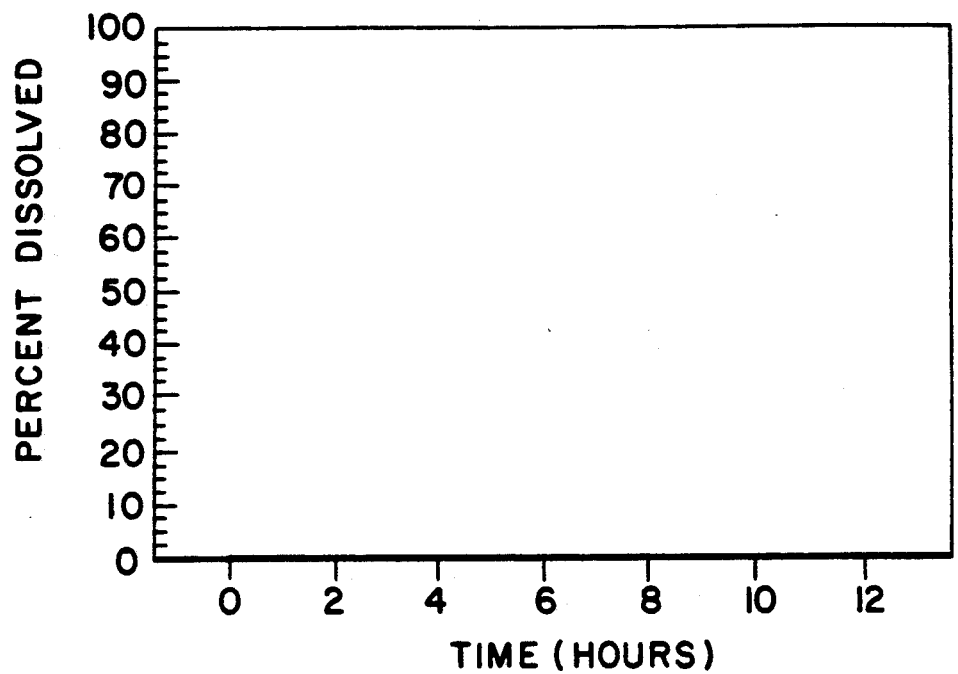
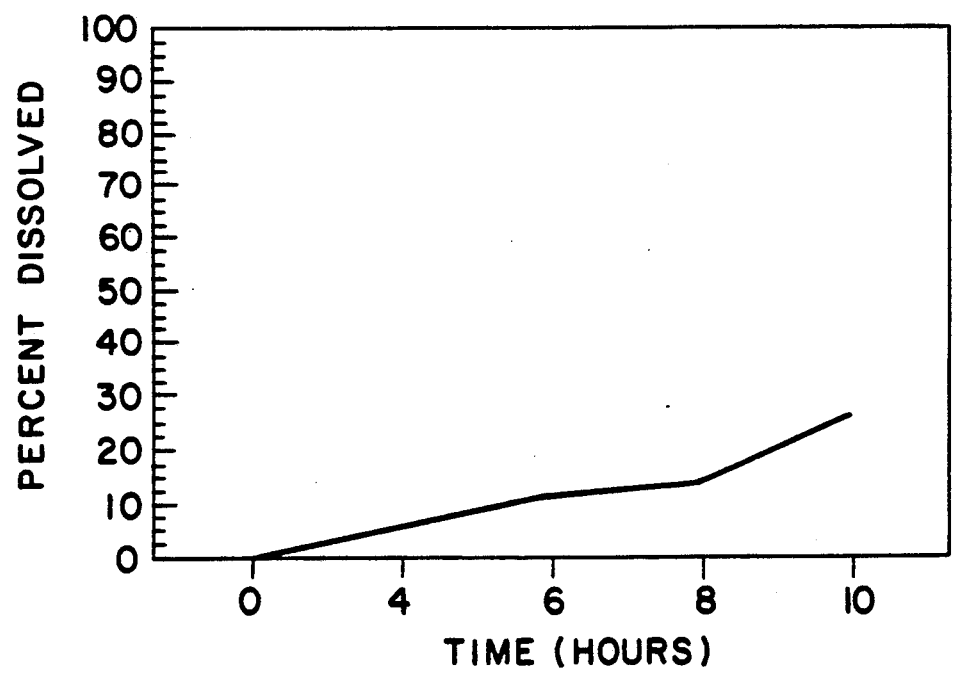
FIG. 14

CONTROLLED RELEASE DEVICE WITH AN IMPERMEABLE COATING HAVING AN ORIFICE FOR RELEASE OF DRUG

THE FIELD OF THE INVENTION

The present invention relates to a device having an impermeable coating with an orifice leading to a core which contains an active agent. When exposed to an environmental fluid, the active agent is released from the core of the device through an orifice into the environment of use over an extended period of time.

BACKGROUND OF INVENTION

In the pharmaceutical and agricultural fields among others, it is often desirable to maintain the concentration of an active agent at a predetermined site for an extended period of time.

For example, in order to maintain a desired concentration of a pharmaceutical composition within a human or animal patient, i.e. within the bloodstream, with a composition administered orally in tablet form, the tablets must be administered regularly. This requirement stems from the fact that, typically, the pharmaceutical composition contained within a tablet is released at once, when the tablet is dissolved in the recipients stomach. Any interruption in the supply of tablets causes a consequent reduction in the concentration of pharmaceutical composition in the blood.

A controlled release tablet releases a pharmaceutical composition in a controlled fashion such that a pharmaceutical composition is released into a patient's stomach at a constant rate for many hours. The rate may be set so as to maintain the desired concentration of pharmaceutical composition in the patient and, the tablet may contain a sufficient amount of said composition to maintain the desired concentration for twelve or more hours. Thus, there is no need for a patient to take tablets both regularly and frequently and the probability of an interruption in a patient's regime is reduced.

Many different devices have been developed to accomplish this result. One such device provides a controlled release via a core tablet including an active agent coated with a semipermeable membrane which has a microscopic passageway therein.

Representative of such a system is U.S. Pat. No. 3,845,770 (Theeuwes et al.). The semipermeable membrane is permeable only to a fluid present in the environment of use (i.e., water), and either the active agent or another component (e.g., sodium chloride) of the core tablet exhibits osmotic activity. Water permeates through the semipermeable membrane due to the presence of the osmotic agent in the tablet core and solubilizes the core. The osmotic pressure differential brings about the release of the active agent through the passageway. The rate of release is said to be dependent upon the permeability of the semipermeable membrane and the osmotic pressure gradient across the semipermeable membrane.

U.S. Pat. No. 4,624,847 (Ayer et al.) describes an osmotic dispensing device wherein a drug is in a compartment surrounded by a semipermeable wall with an osmotic passageway to the compartment. The drug is mixed with an osmopolymer or a with an osmopolymer and an osmagent. The osmopolymer is, for instance a swellable hydrogel which exhibits an osmotic pressure gradient across the semipermeable wall against an external fluid in an environment of use and it imbibes external fluid through the semipermeable wall into the compartment. The osmagent is a salt such as sodium chloride. The osmagent is soluble in the external fluid and, for example, also exhibits an osmotic pressure gradient across the semipermeable wall against the external fluid.

Other patents describing various osmotic dispensing devices having a semipermeable membrane and a passageway through the semipermeable membrane include U.S. Pat. No. 4,519,801 (Edgren); U.S. Pat. No. 4,111,203 (Theeuwes); U.S. Pat. No. 4,777,049 (Magruder et al.); U.S. Pat. No. 4,612,008 (Wong et al.); U.S. Pat. No. 4,610,686 (Ayer et al.); U.S. Pat. No. 4,036,227 (Zaffaroni et al.); U.S. Pat. No. 4,553,973 (Edgren); U.S. Pat. No. 4,077,407 (Theeuwes et al.); and U.S. Pat. No. 4,609,374 (Ayer).

U.S. Pat. No. 4,218,433 (Kooichi et al.) describes another tablet which is said to release active component at a constant rate. A tablet containing a water-soluble component and having a coating which is insoluble in water but has water permeability is formed with an indentation in its surface. When exposed to water, a very small space is said to form between the coating and the indentation, and the coating becomes porous and allows the active component to elute out.

Other devices, such as that described in U.S. Pat. No. 4,687,660 (Baker et al.) provide an osmotic dispensing device which does not use a preformed single passageway to release water-soluble drugs. The device includes a core where drug is combined with excipient and an osmotic enhancing agent. The core is film coated with a solution of a water insoluble, water permeable polymer, a water-permeability enhancing agent such as a polyhydric alcohol, and a water-soluble, polymer-solvent-insoluble, particulate pore-forming material such as lactose. In use, the lactose is leached out as water is imbibed through the film coating. The water dissolves the drug and the osmotic enhancing agent, thereby creating an osmotic gradient.

U.S. Pat. No. 4,816,262 (McMullen) relates to a controlled release tablet having a disc-like configuration with a cylindrical hole extending centrally therethrough which is said to allow for zero order or constant release. The core is a compressed mixture of an active agent and a hydrophilic releasing agent is defined by centrally tapering upper and lower annular faces and outer and inner cylindrical faces. The core is covered with a hydrophobic coating which extends over the upper and lower faces as well as the outer face. Release of the active agent is affected only through a "hole" which comprises the inner cylindrical face.

U.S. Pat. No. 4,814,183 (Zentner) relates to a controlled release device having a core containing a charged resin and a diffusible water soluble ionizable drug having the same charge as the resin. The core is surrounded by a water insoluble wall formed of semipermeable material which is substantially impermeable to core components and permeable to the passage of an external fluid in the environment of use. The wall has one or more holes for release of the drug. The external fluid actuates the migration of drug away from the charged resin and through the hole.

Other devices have been designed with an impermeable coating covering various portions of the device. For example, U.S. Pat. No. 4,814,182 (Graham et al.) relates to a controlled release device comprising an active ingredient/ hydrogel mixture with at least one surface of the device having a coating which is impermeable to aqueous media. U.S. Pat. No. 4,792,448 (Ranade) relates to a cylindrical tablet or bolus having an active ingredient blended with inert excipients and formed into a cylindrical tablet preferably having a flat cylindrical side and a convex top and bottom. The core is covered with an impermeable coating from which strips of the coating have been removed. U.S. Pat. No. 4,803,076 (Ranade) relates to a controlled release device having an active agent contained within a substantially impermeable coating on the base and side but not the top of a truncated cone.

In "Zero-Order Controlled-Release Polymer Matrices for Micro-and Macromolecules", D. Hsieh et al., J. Pharm. Sciences, Vol. 72, No. 1 (January 1983), a hemispherical polymer-drug matrix laminated with an impermeable coating except for an exposed cavity in the center face is described. The hemispherical devices are made by fusing polyethylene and drug by heating, or by gelation of an ethylene-vinyl acetate copolymer by freezing. The copolymers are then molded into hemispheric pellets with a steel bead press-fitted into a central depression. The pellets were then coated with paraffin or 20% ethylene-vinyl acetate copolymer and the bead removed.

SUMMARY OF THE INVENTION

The present invention relates to a controlled delivery device for an active agent which comprises a core comprising an active agent and an outer coating covering said core which includes an orifice communicating from the environment of use to the core for allowing the release of the active agent into the environment of use. The thickness of the coating is adapted such that it is substantially impermeable to the release of the active agent during a predetermined dispensing period.

The outer coating may be comprised of any acceptable material which can be adapted to provide the above-mentioned properties. Thus, a material may be suitable for use as the outer coating even if it is somewhat soluble in or somewhat permeable to the surrounding external fluid, as long as a sufficiently thick coating is applied such that the external fluid does not contact the core except through the orifice for a period sufficient to allow substantially all of the active agent to be released through the orifice.

The outer coating may be chosen so as to eventually dissolve in the external fluid, or be degraded thereby after substantially all of the active agent has been released from the device.

The active agent may comprise a wide variety of chemical compounds or compositions, and may have a wide range of solubilities in the external fluid. The active agent may be combined with one or more excipients to form the core in order to solubilize the core when it is exposed to the external fluid, in order to provide bulk to the core, etc. Conventional tableting excipients can be used to form the core of a tablet in accordance with the present invention. Even freely soluble excipients such as sugars which would not normally be expected to have a role in a sustained release system may be employed.

In a preferred embodiment, the active agent is soluble in the external fluid, or the composition is errodable and therefore capable of being carried out of the device as a suspension. Preferably, the components of the core are solid when dry.

In one embodiment of the present invention, the device is a hemispherical or near-hemispherical tablet with a hole located centrally in the flat or shallow convex side. In another embodiment, the device is a biconvex tablet with at least one concentric hole.

BRIEF DESCRIPTION OF THE DRAWINGS

The following drawings are illustrative of embodiments of the invention and are not meant to limit the scope of the invention as encompassed by the claims.

FIGS. 1–3 are graphical representations of the dissolution curves provided by the biconvex tablets of Examples 1–3 without an orifice;

FIGS. 4–6 are graphical representations of the dissolution curves provided by the biconvex tablets of Examples 1–3 having a 1.59 mm diameter orifice;

FIG. 7 is a graphical representation of the average dissolution curve provided by the biconvex tablets of Example 4 having a 2.38 mm diameter orifice;

FIG. 8 is a graphical representation of the average dissolution curve provided by the biconvex tablets of Example 5 having a 2.78 mm orifice;

FIG. 9 is a graphical representation of the average dissolution curve provided by the biconvex tablets of Example 6 having three 1.59 mm diameter orifices in a convex face thereof;

FIG. 10 is a graphical representation of the average dissolution curve provided by the biconvex tablets of Example 7 having two 1.59 mm diameter orifices in a convex face thereof;

FIG. 11 is a graphical representation of the average dissolution curve provided by the biconvex tablets of Example 8 having one 1.59 mm diameter orifice centrally made in each convex face;

FIG. 12 is a graphical representation of the dissolution curve provided by the biconvex tablet of Example 9 having one 1.59 mm diameter orifice;

FIG. 13 is a graphical representation of the dissolution curve provided by the biconvex tablet of Example 10 without an orifice;

FIG. 14 is a graphical representation of the dissolution curve provided by the biconvex tablet of Example 10 having one 1.59 mm diameter orifice;

DETAILED DESCRIPTION

Figure 15:
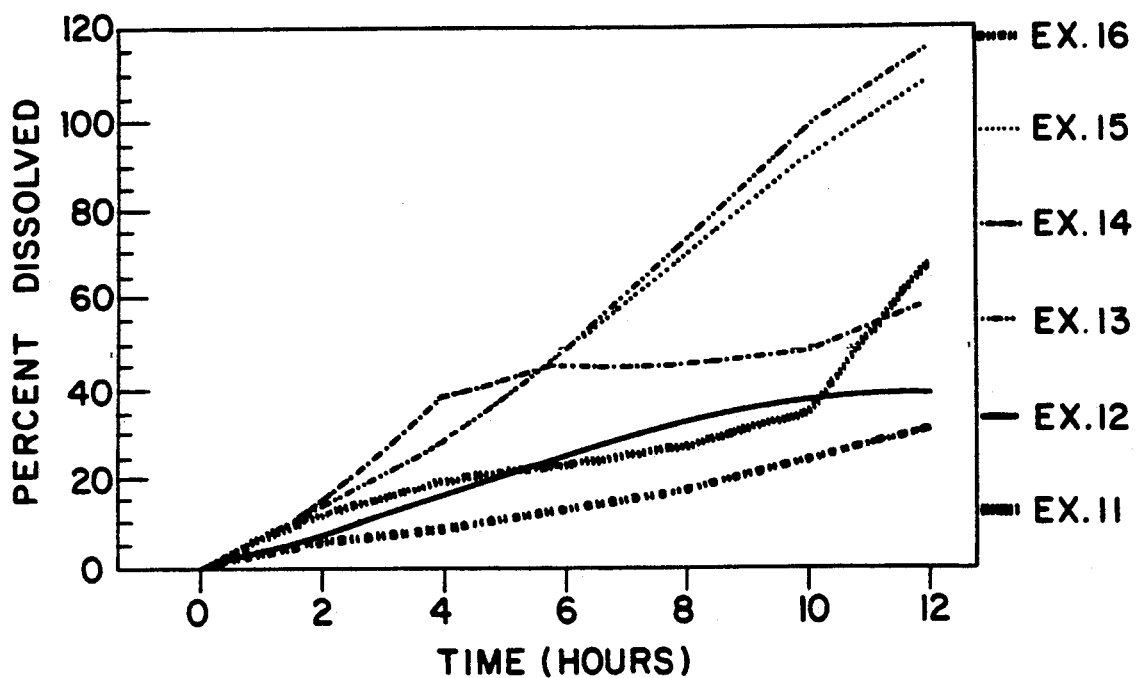
FIG. 15 is a graphical representation of the dissolution curve provided by the near-hemispherically shaped tablets of Examples 11–16.

The core of the device of the present invention may be prepared using conventional tablet excipients and formulation methods. Depending upon the solubility and the amount of active agent to be included in the core, any generally accepted soluble or insoluble inert pharmaceutical filler (diluent) material may be used to bulk up the core or to solubilize the active agent. These materials include but are not limited to sucrose, dextrose, lactose, fructose, xylitol, mannitol, sorbitol, dicalcium phosphate, calcium sulfate, calcium carbonate, starches, cellulose, polyethylene glycols, polyvinylpyrollidones, polyvinyl alcohols, sodium or potassium carboxmethylcelluloses, gelatins, mixtures of any of the above, and the like. In addition, it is possible to directly compress an active agent with a small amount of lubricant when the active agent is soluble in the external fluid and is included in such an amount to provide a suitably sized core.

It is preferred that a lubricant be mixed with the active agent and excipients prior to compression into a solid core. Any generally accepted pharmaceutical lubricant, including calcium or magnesium soaps may be used. Most preferred is magnesium stearate in an amount of about 0.25-5 percent by weight of the core.

Active agents can be formulated with a small amount of a binder material such as, for example, gelatin or polyvinylpyrollidone (i.e. 94-99.75% of the core comprises the active agent). In such cases, the components of the core may be subjected to wet granulation. Highly soluble pharmaceutically active compounds such as potassium chloride may be directly compressed into an acceptable core with the inclusion of 0.25 percent magnesium stearate without being in admixture with an excipient.

The particular excipient chosen is dependent in part upon the solubility of the active agent in the environmental fluid. The ratio of active agent to excipient is based in part upon relative solubility of the active agent in the external fluid and the desired rate of release. If the active agent is relatively soluble, it may be desirable to slow down the erroding of the core by using a relatively insoluble excipient such as dicalcium phosphate.

The complete mixture of active agent, lubricant, excipient, etc., in an amount sufficient to make a uniform batch of cores, is subjected to compression in a conventional production scale tableting machine at normal compression pressures, i.e. about 2000-16000 lbs/sq. in.

The term "active agent" is defined for purposes of the present invention as any chemical substance or composition which can be delivered from the device into an environment of use to obtain a desired result. The active agent can be soluble in the external fluid which enters the device through the orifice, or it can have limited solubility in the external fluid. Preferably, an excipient which is readily soluble in the external fluid is induced when the active agent has limited solubility in the external fluid. When the active agent is relatively soluble in the external fluid, the choice of excipient is less critical to obtaining a desired controlled release pattern. The active agent may be a drug, pesticide, herbicide, fertilizer, anti-fouling agent, nutrient, preservative, catalyst, etc.

When the active agent is a biologically active drug which is taken orally and the external fluid is gastric fluid, it is preferred that the drug exhibits a between the solubility defined in the United States Pharmacopeia (USP) XXI, page 7 as "freely soluble" (i.e., 1-10 parts solvent per 1 part solute) and "sparingly soluble" (i.e., 30-1000 parts solvent per 1 part solute).

An example of a drug which is considered freely soluble for the purposes of the present invention is chlorpheniramine maleate. An example of a sparingly soluble drug is theophylline. Examples of other drugs which have solubilities falling within these approximate parameters may be determined from any number of sources, such as the Solubility Reference Table found in the USP XXI, pages 1484-9.

The device of the present invention can be used in conjunction with a wide range of drugs and is especially well-suited for drugs having a wide therapeutic window, since precise dosing is not very critical for the same. The therapeutic window is commonly defined as the difference between the minimum effective blood concentration and the maximum effective blood concentration and the toxic concentration of the drug.

Generally, examples of drugs which can be used in accordance with the present invention include analgesics, antihistamines decongestants, laxatives, antacids, vitamins, anti-infectives, anti-inflammatories, antimicrobials, vasoconstrictors, vasodilators, psychotropics, stimulants including appetite suppressants, diuretics, anti-asthmatics, diuretics, anti-spasmodics, antidiarrheals, expectorants, mucolytics, cough suppressants, hypnotics, psychotropics, sedatives, hypoglycemics, hyperglycemics and others.

The compacted masses which comprise the cores are then coated with a suitable amount of a material such that the coating is substantially impermeable to the environmental fluid during the desired release time. Representative materials suitable for use as the coating include those materials commonly considered to be insoluble in the art, such as ethyl cellulose, acrylate polymers, polyamides (nylons), polymethacrylates, polyalkenes (polyethylene, polypropylene), bio-degradable polymers (including homo- or hetero-polymers of polyhydroxy butyric or valeric acids and homo or hetero-polymers of polylactic, polyglycolic, polybutyric, polyvaleric, and polycaprolactic acids), waxes, natural oils, other hydrophobic insoluble materials such as polydimethylsiloxane, hydrophilic materials such as cross-linked sodium carboxymethyl cellulose and cross-linked sodium or uncross-linked carboxy-methyl starch. Many other polymers considered to be relatively insoluble would also be useful in the present invention.

While some of the above materials do exhibit a certain degree of permeability to environmental fluids such as water, the coating is applied at such a thickness that they do not expose the core to the environmental fluid and are not removed by dissolution or otherwise disrupted before the desired duration of the controlled release of the active agent has passed. Thus, for example, while ethylcellulose has in the past been used as a coating for devices such as pharmaceutical controlled release tablets, the thickness of the ethyl cellulose coating has generally been in the neighborhood of 4 percent by weight of the tablet core and possibly containing a proportion of a soluble polymer, e.g. hydroxypropylmethylcellulose and/or a plasticizer, e.g. glycerol. In contrast, the ethyl cellulose coat of the present invention in such circumstances would generally be 2-3 times thicker (i.e. 10-12 percent or more by weight of the tablet core).

It is also possible to use relatively thick coatings of materials which are considered in the art to be relatively soluble in, environmental fluid, such as polyvinylpyrrolidone, cellulose ethers including hydroxypropylmethylcellulose, methylcellulose, hydroxyethylcellulose, hydroxypropylcellulose, etc., sodium carboxymethyl cellulose, sodium carboxymethyl starch and enteric materials (such as cellulose acetate phthallate, polyvinylalcohol phthallate, shellac, zein, hydroxypropylmethyl cellulose phthallate, cellulose acetate trimaleate, etc).

It is also possible to use coatings comprising combinations of relatively insoluble and relatively soluble materials. The thickness of the coating necessary to provide results in accordance with the present invention may be simply determined by one of ordinary skilled in the art via the preparation of devices with differing coating thicknesses, performing dissolution tests in the devices without the inclusion of an orifice in the device, and choosing the coating thickness which does not allow the release of the active agent from the device during the desired duration of controlled release.

In one preferred embodiment, the impermeable coating comprises ethyl cellulose. In another preferred embodiment, the impermeable coating comprises from about 90 to about 96.5 percent hydrogenated vegetable oil, from about 3 to about 5 percent polyvinylpyrrolidone, and from about 0.5 to about 5 percent magnesium stearate or other similar lubricant.

The impermeable coating may be formed by film formation from a polymer in solution, or suspension using pouring or spraying onto a pre-formed tablet core. Preferably this process is carried out by spraying the coating onto the tablet core in a rotating pan coater or in a fluidized bed coater until the desired coating thickness is achieved. Alternatively, a tablet core may be dip coated or melt coated. This is especially useful with waxes and oils. In another embodiment, the core may be compression coated. In other words, a suitable impermeable coating material may be pressed onto a preformed tablet core.

In a preferred embodiment, an adhesive coat such as shellac or polyvinyl acetate phthallate (PVAP) is applied to the core prior to applying the impermeable coating in order to improve adhesion of the impermeable coating to the core.

Next, an orifice is made in the coated device. For purposes of the present invention, the term "orifice" is synonymous with hole, passageway, outlet, aperture, etc. The orifice may be formed using any technique known in the art. For instance, the orifice may be made using a needle or other form of boring instrument such as a mechanical drill or a laser to remove a section of the impermeable layer of the tablet core. Alternatively, the impermeable layer may be prevented from covering a patch of a pre-formed core to thereby provide an orifice. This may be achieved using chemical protection or a modified coating method. If compression coating is employed, an eccentric or assymetrical core may be employed so that the core automatically reveals a portion of its surface, as the impermeable layer is compressed thereon. Alternatively, a specially designed punch tip may be incorporated into the compressing equipment, in order to pierce through the impermeable layer at the point of compaction.

It is preferred that the orifice extend through the entire impermeable layer such that there is immediate exposure of the core to the environmental fluid when the device is placed in the desired environment of use.

The orifice is made in the sealed device so that the active agent is released from the device at the desired rate. The desired rate of release is achieved by providing the proper diameter of the orifice relative to the diameter of the device and taking into account parameters such as the properties of the active agent and the excipients used (if any). Such properties include solubility, matrix formation, etc. Preferably, the orifice is dimensioned to allow the entrance of environmental fluid (e.g., gastric fluid) such that the active agent is released from the device at a predetermined controlled rate.

The device of the present invention may be of any preselected shape, such as biconvex, hemispherical or near-hemispherical, oval, oblong, round, cylindrical, triangular, etc. However, it is presently preferred that the device is biconvex, hemispherical, or near-hemispherical. By "near-hemispherical", it is meant that one face of the device is substantially flat, shallow convex or shallow concave, and the opposite face is deeply convex (i.e., the deeply convex face has a greater radius of curvature than the shallow convex, shallow concave, or substantially flat face). It is most preferred presently that the device is biconvex due to complexities involved with the coating of hemispherical or near-hemispherical devices.

The orifice can have any shape, including round, triangular, square, elliptical, irregular, and the like. However, for purposes of reproducibility, it is preferred that the orifice be round. Similarly, the orifice may be located at any point on the coated surface of the device, but reproducibility has been found to be substantially improved when the orifice is centrally located. For example, reproducibility has been found to be improved when a biconvex tablet according to the present invention includes a concentrically located orifice rather than an orifice that is eccentric or in the side wall of the tablet.

In other embodiments of the present invention, more than one orifice may be provided in the device for the release of active agent. The orifices may be located on the same face of the tablet, or on different faces.

The orifice has a diameter which normally corresponds to from about 10 to about 60 percent of the diameter of the device. Preferably, the orifice has a diameter which is about 30 percent of the diameter of the device. On the other hand, the device may be provided with a number of orifices, the sum of whose diameters comprise about the same diameter as a single orifice which has been determined to provide an acceptable release rate. Of course, the diameter of the orifice is dependent in part upon the active agent and the desired release rate. In cases where the orifice is non-circular, the orifice will correspond to from 1 to about 40 percent of the corresponding surface of the device, and preferably about 10 percent.

The device of the present invention is preferably an oral tablet, although it may be adapted for buccal, cervical, rectal, intrauterine, nasal, artificial gland, implant use and the like. When the device is an implant, it is preferable that the impermeable coating is either physiologically inert or biodegradable. The device also can be sized, shaped structured and adapted for delivering an active agent in streams, aquariums, fields, factories, reservoirs, laboratory facilities, hot houses, transportation means, naval means, for veterinary use, chemical reactions and other environments of use.

The amount of agent present in the device, whether soluble in the environmental fluid or a derivitized soluble form thereof, is generally non-limited and it is an amount larger than or equal to the amount of agent that is necessary to be effective for bringing about the desired effect upon its release in the environment of use. Since the invention contemplates a variety of uses, there is no critical upper limit on the amount of agent incorporated in the device. The lower limit will depend on the span of the release of the product and the activity of the product.

In the case of an orally taken biconvex tablet, once the tablet is exposed to the gastric fluid within the stomach, the drug and any excipient is dissolved via gastric fluid which passes through the orifice and contacts the exposed portion of the tablet core. The rate of release of drug through the orifice remains constant as the drug and excipient is continually erroded, in part because the exposed surface of the drug and excipient moves away from the orifice and simultaneously increases the surface area of exposed core.

In certain embodiments of the present invention, it may be advantageous to include one or more release modifying agents in the tablet core which aids in the release of the active agent from the device in the environment of use. For example, the inclusion of a surfactant or an effervescent base may be helpful in certain cases to overcome surface tension effects, etc. Other releasing modifying agents known as osmagents osmotically deliver the active agent from the device by providing an osmotic pressure gradient against the external fluid. Such agents are particularly useful when the active agent has limited solubility in the environment of use. Still other release modifying agents are swelling agents provided in an amount sufficient to facilitate the entry of the environmental fluid without causing the disruption of the impermeable coating. Alternatively, release modifying agents may be used to slow the release of active agent from the device. Examples of such agents include hydrophobic materials and insoluble polymers. Other release modifying agents which may be used in conjunction with the present invention include ion exchange resins.

Surfactants useful as release modifying agents in the present invention can be anionic, cationic, nonionic, or amphoteric. Examples include sodium lauryl sulfate, sodium dodecyl sulfate, sorbitan esters, polysorbates, pluronics, potassium laurate, and the like.

Effervescent bases useful as release modifying agents in the present invention include sodium glycine carbonate, sodium carbonate, potassium carbonate, sodium bicarbonate, potassium bicarbonate, calcium bicarbonate, and the like.

Osmagents useful as release modifying agents in the present invention include, for example, sodium chloride, calcium chloride, calcium lactate, sodium sulfate, lactose, glucose, sucrose, mannitol, urea, and many other organic and inorganic compounds known in the art.

Examples of suitable swelling agents include synthetic gums such as hydroxypropylmethylcelluloses (HPMC) hydroxypropyl cellulose, carboxymethyl cellulose, and natural gums such as xanthan gum, locust bean gum, acacia, tragacanth, guar gum, carrageenan, and propylene glycol alginate.

Examples of suitable hydrophobic materials useful as release modifying agents include vegetable oils such as hydrogenated cottonseed oil, hydrogenated castor oil, and the like. Examples of insoluble polymers include ethyl cellulose, etc.

Other release modifying agents which may be useful in the present invention provide a soluble or insoluble polymer backbone to the core. Such agents may decrease unequal density areas of the core formed during the compression molding of the same. Suitable soluble polymers which may be incorporated into the core include those which melt upon compression and fuse upon cooling to provide nearly uniform cross-sectional density, such as polyethylene glycols having a molecular weight of from about 6 to about 20,000 and the like. Other water soluble polymers are sufficiently viscous upon contacting the front of environmental fluid which enters through the orifice to provide the same effect, such as high molecular weight polyvinylpyrrolidone (i.e., K90 grade commercially available from GAF Corporation and having a molecular weight of about 360,000).

In another embodiment of the present invention, the device may be multi-layered and preferably bi- or tri-layered. This may be desirable, for example in order to provide a loading dose of an active agent, or for releasing two or more different agents.

By means of the present invention, it is possible to obtain a zero-order release of a pharmaceutical composition, or other active agent, i.e., a constant amount of drug is released per unit time in vitro by erosion of the tablet core. On the other hand, the device may be designed such that the rate of release of the active agent varies with time which may be used to achieve a chronotherapeutic effect not normally possible with sustained release devices. This is in addition to the other parameters of the present invention that govern the rate of release, such as the size and location of the orifice.

DETAILED DESCRIPTION OF THE PREFERRED EMBODIMENT

The following examples illustrate various aspects of the present invention. They are not to be construed to limit the claims in any manner whatsoever.

EXAMPLE 1-3

The coating thickness necessary to prevent an active agent present in the core of a biconvex tablet from being released during the desired duration treatment is determined as follows.

Tablet cores are formulated by mixing 6 percent chlorpheniramine maleate, 93.5 percent Fast Flo ® lactose (commercially available from Foremost Whey Products, Wisconsin, USA) and 0.5 percent magnesium stearate. The mixture is compressed into 7.9 mm standard biconvex cores. Each core weighs an average of about 200 mg and has a hardness of about 10.29 kp.

A coating formulation is also prepared by blending 59.3 percent ethyl cellulose (Surelease ®, an aqueous latex ethyl cellulose with a diethylphthallate plasticizer, commercially available from Colorcon, Inc.), 39.9 percent distilled water, and 0.8 percent Syloid 244 ® (fumed silica commercially available from Davison Chemicals, Baltimore, Md., USA; added to prevent the coated tablets from sticking together) into a homogeneous blend.

The tablet cores (total weight of about 1 kg) are loaded into a tablet coating pan and preheated for 4-5 minutes using a hot air stream. The tablet cores were then coated in a conventional rotating pan by spraying from above with the coating polymer until each core is covered by a uniform coat of ethyl cellulose.

The tablets of Example 1 are removed after about 500 g of coating solution is added, such that the weight of the coating corresponds to about 6.4 percent of the coated tablet by weight.

The tablets of Example 2 are removed after 750 g of coating solution is added, such that the weight of the coating corresponds to about 11 percent of the coated tablet by weight.

The tablets of Example 3 are removed after about 1000 g of coating solution is added, such that the weight of the coating corresponds to about 12.4 percent of the coated tablet by weight.

Next, six tablets from Example 1 and three tablets from each of Examples 2 and 3 are tested in an automated USP dissolution apparatus for dissolution in distilled water. The data is represented as the percentage of chlorpheniramine maleate released versus time. The tablets of Example 1 (6.4 percent coating) release in excess of 14 percent of the chlorpheniramine maleate in 6 hours and 23 percent in 12 hours. The tablets of Example 2 (11 percent coating) release about 34.85 percent of the chlorpheniramine maleate in 6 hours and about 43.21 percent of the chlorpheniramine maleate in 12 hours. In contrast, the tablets of Example 3 (12.4 percent coating) released only 2 percent of the chlorpheniramine maleate over 12 hours. The average results for the tablets tested from Examples 1-3 are provided in FIGS. 1-3, respectively.

Next, 1.59 mm diameter orifices are manually made using a drill bit centrally in one of the convex walls of the biconvex tablets taken from Examples 1-3. The orifices extend completely through the coating but do not penetrate the tablet core.

Six tablets from Example 1 (6.4 percent coating) and three tablets each from Example 2 (11.0 percent coating) and Example 3 (12.4 percent coating) are subjected to dissolution testing. The results are graphically presented in FIGS. 4-6, respectively. The graphically depicted results show a marked increase in release of chlorpheniramine maleate from the tablets having the orifice. In Examples 1 and 2, the release of chlorpheniramine maleate is in part due to the release of the drug through the orifice and in part due to the passage of the drug through the coating. In contrast, in Example 3, virtually all of the drug released is via the orifice.

EXAMPLES 4-9

In Examples 4-9, biconvex tablets are prepared according to the method described for Example 2 (12.4 percent coating), except that the diameter of the orifice and the number of orifices are varied.

In Example 4, a 2.38 mm diameter orifice is centrally made in a convex face of six biconvex tablets. The tablets are then subjected to dissolution testing. The results are graphically presented in FIG. 7.

In Example 5, a 2.78 mm diameter orifice is centrally made in a convex face of six biconvex tablets. The tablets are then subjected to dissolution testing. The average results are graphically presented in FIG. 8. Comparing the results to the results obtained from Example 3, it appears that even though the orifice is larger, the amount of drug released is not increased. It therefore appears that there is a limiting condition present. One possible explanation for this effect is that at a certain point, the solubility of the drug limits its release through the orifice.

In Example 6, three 1.59 mm inch diameter orifices are centrally made in a convex face of six biconvex tablets. The tablets are then subjected to dissolution testing. The average results are graphically presented in FIG. 9.

In Example 7, two 1.59 mm diameter orifices are centrally made in a convex face of six biconvex tablets. The tablets are then subjected to dissolution testing. The average results are graphically presented in FIG. 10.

In Example 8, a 1.59 mm diameter orifice is centrally made in each convex face of six biconvex tablets. The tablets are then subjected to dissolution testing. The average results are graphically presented in FIG. 11.

In Example 9, a biconvex tablet is prepared according to the method described for Example 3, except that the tablet core is coated with Aquacoat ® (an aqueous latex ethyl cellulose commercially available from FMC Corporation). The coating corresponds to about 11.8 percent of the core by weight. One 1.59 mm diameter orifice is centrally made in each convex face. A representative tablet is then subjected to dissolution testing. The results are graphically presented in FIG. 12.

EXAMPLE 10

Tablet cores are formulated by mixing 6 percent chlorpheniramine maleate, 93.25 percent dicalcium phosphate (Emcompress ®, commercially available from Edward Mendell Co., Inc.) and 0.75 percent magnesium stearate. The mixture is compressed into biconvex cores weighing an average of 200 mg.

The tablet cores are then coated with a subcoating of shellac dissolved in ethanol such that the weight of the subcoat corresponds to about 4 percent of the coated tablet by weight. Next, a coating of Surelease ® is applied to the tablet cores such that the coating corresponds to about 13.1 percent of the coated tablet by weight. A representative tablet is then subject to dissolution testing. The results are graphically presented in FIG. 13. As is readily apparent, little or no chlorpheniramine maleate is released over the 12 hour dissolution period.

Next, a 1.59 mm diameter orifice is centrally made in a convex face of a representative tablet. The dissolution profile of the tablet is graphically presented in FIG. 14. About 28 percent of the chlorpheniramine maleate is released over the 12 hour dissolution period.

EXAMPLES 11-16

Examples 11-16 illustrate the effect of different shapes and sizes of tablets prepared according to the present invention having one orifice. In each of Examples 11-16, the tablet cores are formulated by mixing 6 percent chlorpheniramine maleate, 93.5 percent Fast Flo ® lactose, and 0.5 percent magnesium stearate. In each of these Examples, the tablet cores are then coated with Surelease ®.

In Example 11, the tablet core is compressed with both faces flat faced. The tablet core weighs 198 mg, is 5 mm in diameter and 7.05 mm thick. The coated tablet weighs 245 mg, is 5.59 mm in diameter and 7.61 mm thick. The coating corresponds to about 19.2 percent of the weight of the coated tablet. A 1.59 mm diameter orifice is centrally made in the flat face.

In Example 12, the tablet core is compressed into a near-hemispherical shape with one face deep convex and the other face shallow convex. The tablet core weighs 198 mg, is 10 mm in diameter and 3.22 mm thick. The coated tablet weighs 238 mg, is 10.55 mm in diameter and 7.61 mm thick. A 2.38 mm diameter orifice is centrally made in the shallow convex face.

In Example 13, the tablet core is compressed into the near-hemispherical shape of Example 12, and has a core weight of 399 mg, is 10 mm in diameter, and 5.12 mm thick. The coated tablet weighs 476 mg, is 10.73 mm in diameter and is 5.64 mm thick. The coating corresponds to about 16.2 percent by weight of the coated tablet. A 2.38 mm orifice is centrally made in the shallow convex face.

In Example 14, the tablet core is compressed into the near-hemispherical shape of Example 12, and has a core weight of 700 mg, is 10 mm in diameter, and 7.8 mm thick. The coated tablet weighs 781 mg, is 10.48 mm in diameter and 8.21 mm thick. The coating corresponds to about 10.4 percent by weight of the coated tablet. A 2.38 mm orifice is centrally made in the shallow convex face.

In Example 15, the tablet core is compressed into the near-hemispherical shape of Example 12 and has a core weight of 396 mg, is 12.7 mm in diameter and 4.35 mm thick. The coated tablet weighs 488 mg, is 13mm in diameter and 4.89 mm thick. The coating corresponds to about 18.9 percent by weight of the coated tablet. A 2.38 mm diameter orifice is centrally made in the shallow convex face.

In Example 16, the tablet core is compressed into the near-hemispherical shape of Example 12 and has a core weight of 806 mg, is 12.7 mm in diameter and 6.86 mm thick. The coated tablet weighs 896 mg, is 13.2 mm in diameter, and is 7.3 mm thick. The coating corresponds to about 10 percent of the weight of the coated tablet. A 2.38 mm diameter orifice is centrally made in the shallow convex face.

Representative tablets of each of Examples 11-16 are subjected to dissolution testing. The results are graphically presented in FIG. 15.

EXAMPLES 17-18

In Example 17, tablet cores are formulated by mixing 8.1 percent propranolol hydrochloride, 10 percent sodium lauryl sulfate (as a release enhancing agent), 81.4 percent Fast Flo ® lactose, and 0.5 percent magnesium stearate. The mixture is compressed into the near-hemispherical shape. The tablet core weighs 410 mg, is 10 mm in diameter and 5.46 mm thick. The tablet is coated with Surelease ®. The coated tablet weighs 501 mg, is 10.79 mm in diameter and 6.1 mm thick. The coating corresponds to about 18 percent by weight of the coated tablet. A 2 38 mm diameter orifice is centrally made in the shallow convex face.

In Example 18, the tablet core includes 8.6 percent propranolol hydrochloride, 5 percent sodium lauryl sulfate, 85.9 percent Fast Flo ® lactose, and 0.5 percent magnesium stearate. The tablet core is compressed into the near-hemispherical shape of Example 12, and has a core weight of 410 mg, is 10 mm in diameter, and 5.4 mm thick. The coated tablet weighs 494 mg, is 10.77 mm in diameter and 5.95 mm thick. The coating corresponds to about 17 percent by weight of the coated tablet). A 2.38 mm diameter orifice is centrally made in the shallow convex face.

Figure 16:
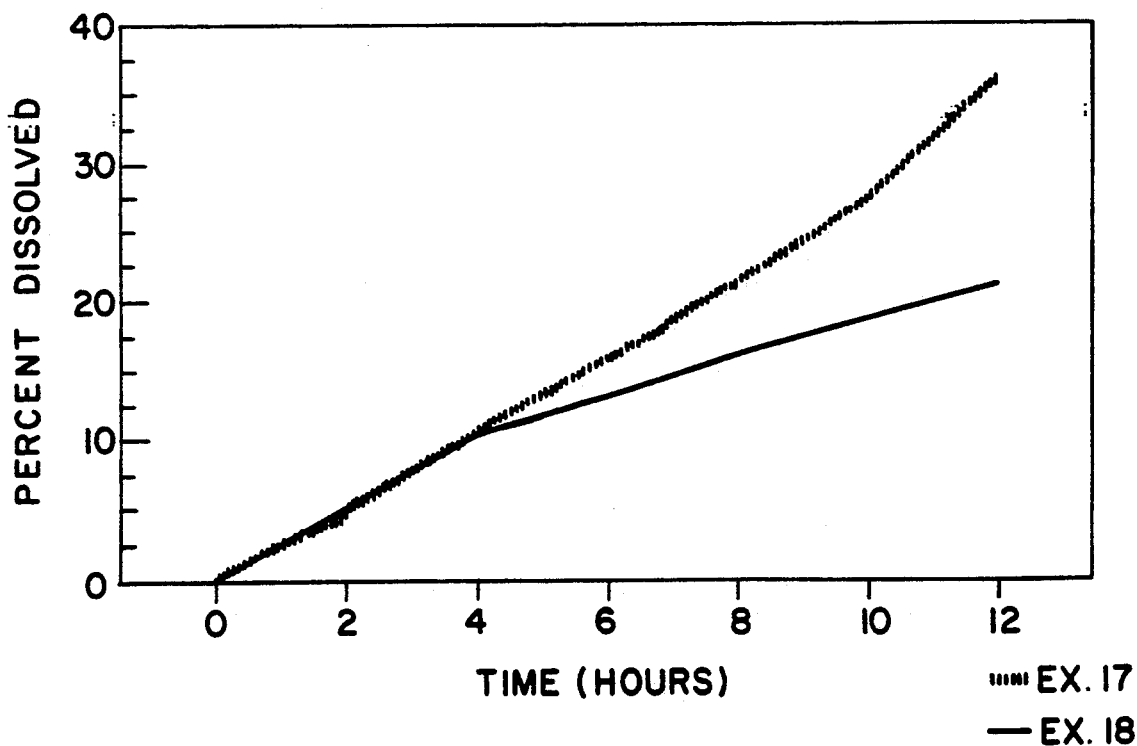
FIG. 16 is a graphical representation of the dissolution curve provided by the near-hemispherically shaped tablets of Examples 17 and 18.

A representative tablet of Examples 17 and 18 is subjected to dissolution testing. The results are graphically presented in FIG. 16.

EXAMPLE 19

In Example 19, the coating is applied to the tablet core by compression rather than spraying, as in previous examples.

Biconvex tablet cores are prepared which include 6 percent chlorpheniramine maleate, 93.5 percent Fast Flo ® lactose, and 0.5 percent magnesium stearate. The tablet core weighs 200mg. The ingredients are compressed into a biconvex tablet core. The compressed tablet core is 5 mm in diameter and 2.5 mm thick.

A coating composition is prepared which includes 95 percent hydrogenated vegetable oil, 3 percent polyvinyl pyrollidone, (grade K90, commercially available from GAF Corporation) and 2 percent magnesium stearate. The polyvinylpyrollidone is added as a binder to make the coating free-flowing. The coating is compression coated onto the tablet cores using a single punch press. The coated tablet weighs about 775 mg. The compression coated tablet is 12.7 mm in diameter and 4.5 mm thick. The coating corresponds to about 74 percent by weight of the coated tablet. A representative tablet is then subjected to dissolution testing.

Figure 17:
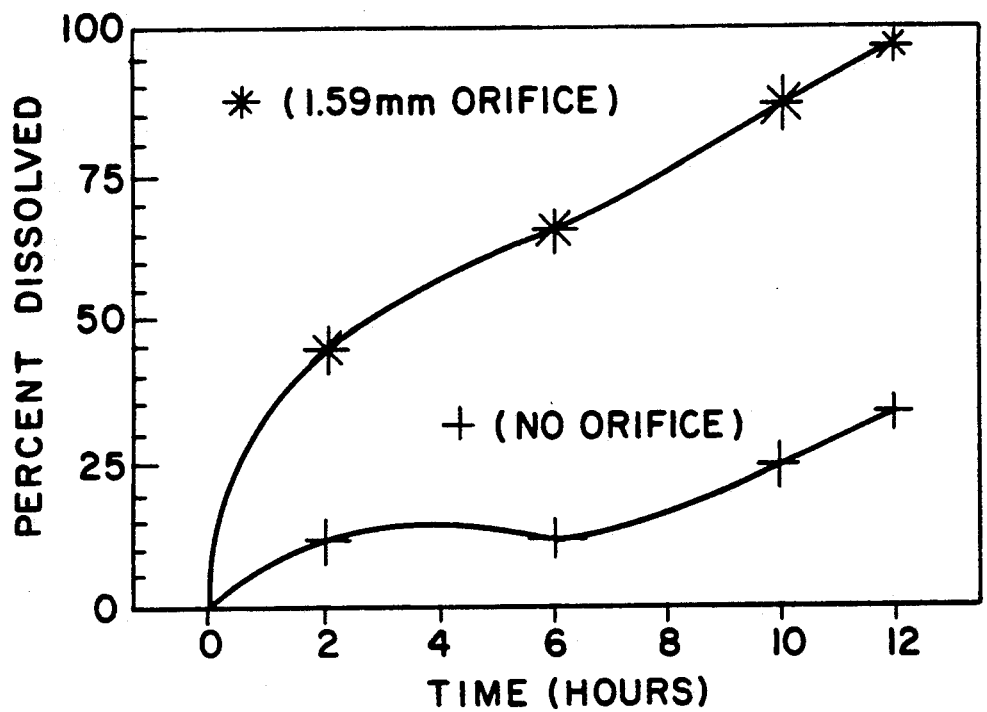
FIG. 17 is a graphical representation of the dissolution curve provided by the biconvex compression-coated tablet of Example 19.

Thereafter, a 1.59 mm diameter orifice is centrally made in one of the convex faces of a representative tablet, and the tablet is subjected to dissolution testing. The results are graphically presented in FIG. 17.

EXAMPLES 20-22

In Examples 20-22, the dissolution profile of tablets having different active ingredients is examined.

In Example 20, a tablet core including 6 percent chlorpheniramine maleate, 93.5 percent Fast Flo ® lactose, and 0.5 percent magnesium stearate is compressed into the near-hemispherical shape of Example 12, and has a core weight of 198 mg, a diameter of 10 mm, and is 3.32 mm thick. The tablet core is coated with Surelease ® such that the coated tablet weighs 238 mg, is 10.55 mm in diameter, and 3.71 mm thick (such that the coating comprises about 10.9 percent of the tablet weight). A 2.38 mm diameter orifice is centrally made in the shallow convex face.

In Example 21, the tablet core includes 9 percent propranolol hydrochloride, 90.4 percent Fast Flo ® lactose, and 0.6 percent magnesium stearate such that the core weighs 202 mg, is 10 mm in diameter and 3.35 mm thick. The tablet is coated with Surelease ®. The coated tablet weights 254 mg, is 10.42 mm in diameter, and 3.83 mm thick (such that the coating weighs about 20.5 percent of the tablet weight). The coating corresponds to about 20.5 percent of the weight of the coated tablet. A 2.38 mm diameter orifice is centrally made in the shallow convex face.

In Example 22, the tablet core includes 12.3 percent phenylpropanolamine, 86.6 percent Fast Flo ® lactose, 0.6 percent magnesium stearate and 0.5 percent fumed silicon dioxide, such that the core weighs 388 mg, is 10 mm in diameter, and 4.94 mm thick. A Surelease ® coating is applied such that the coated tablet weights 456 mg, is 10.62 mm in diameter, and is 5.41 mm thick. The coating corresponds to about 10.9 percent of the weight of the coated tablet. A 2.38 mm diameter orifice is centrally made in the shallow convex face.

Figure 18:
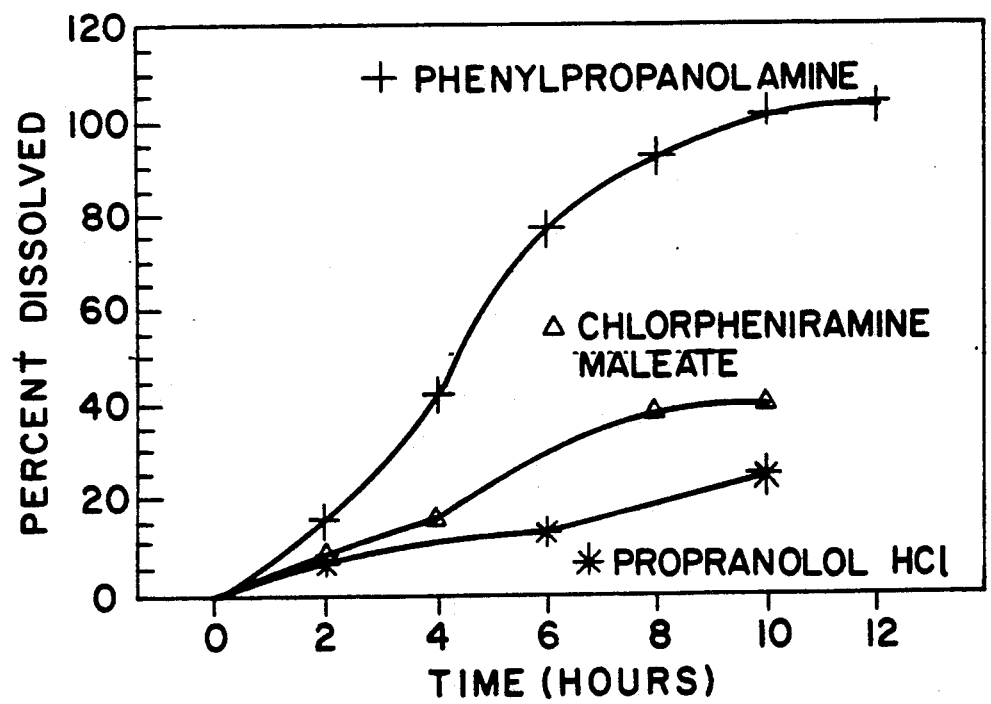
FIG. 18 is a graphical representation of the dissolution curves of the near-hemispherical tablets of Examples 20–22.

Representative tablets of Examples 20-22 are subjected to dissolution testing. The results are graphically presented in FIG. 18.

EXAMPLES 23-24

In Examples 23-24, the effect of tablet shape (biconvex vs. near-hemispherical) is examined.

In Example 23, a tablet core including 6 percent chlorpheniramine maleate, 93.5 percent Fast Flo ® lactose, and 0.5 percent magnesium stearate is compressed into a biconvex tablet core. Thereafter, a coating of Surelease ® is applied such that the coating comprises 12.4 percent of the tablet weight. A 2.38 mm orifice is centrally made in one of the convex faces.

In Example 24, a tablet core also comprises 6 percent chlorpheniramine maleate, 93.5 percent Fast Flo ® lactose, and 0.5 percent magnesium stearate. The ingredients are compressed into the near-hemispherical tablet shape of Example 12. Thereafter, a coating of Surelease ® is applied such that the coating comprises of 10.9 percent of the weight of the tablet. A 2.38 mm orifice is centrally made in the shallow convex face.

Figure 19:
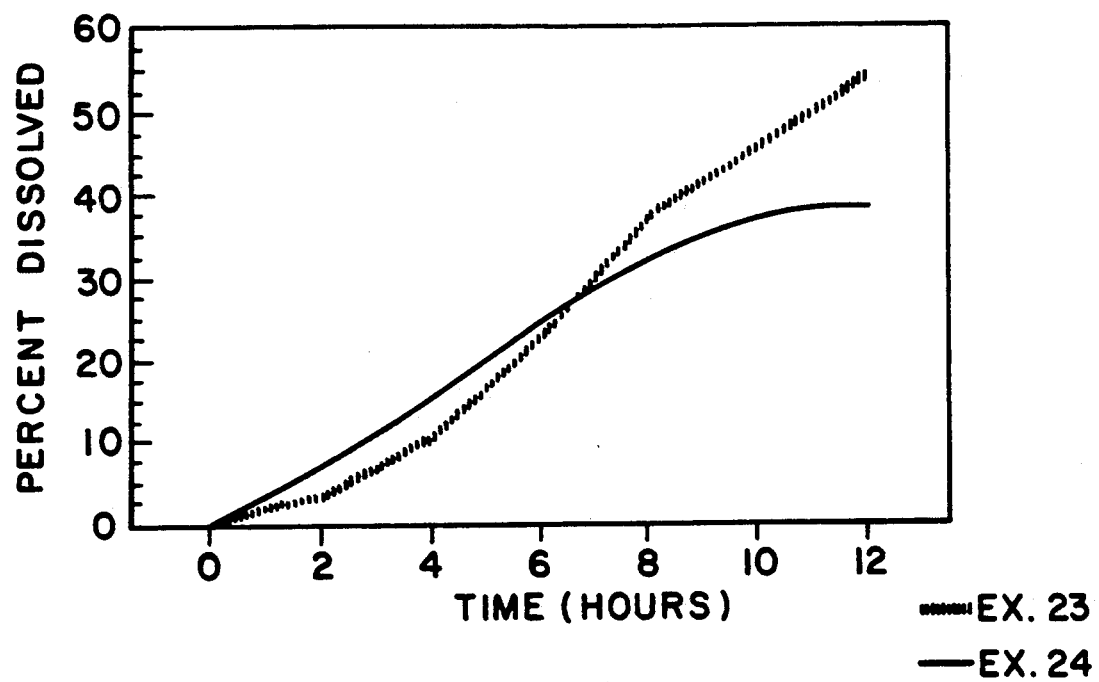
FIG. 19 is a graphical representation comparing the dissolution curves of the biconvex tablet of Example 23 versus the near-hemispherical tablet of Example 24.

Representative tablets of Examples 23 and 24 are subjected to dissolution testing. The results are graphically presented in FIG. 19.

EXAMPLE 25

A bilayered tablet is prepared by preparing a lower, lightly compacted layer in a tablet die including 0.686 mg of tartrazine, followed by compaction of an upper layer directly above the first including 0.686 mg Sulfan Blue BPC 1943 so as to produce a tablet core having 2 discrete layers. The bilayered core weighs 520 mg. Each layer further comprised 0.5 percent magnesium stearate, the remaining mass differential being comprised of Fast Flo ® lactose. A coating comprising Surelease ® is then sprayed onto the tablet core. The total weight of the coated tablet is 582.4 mg.

Figure 20:
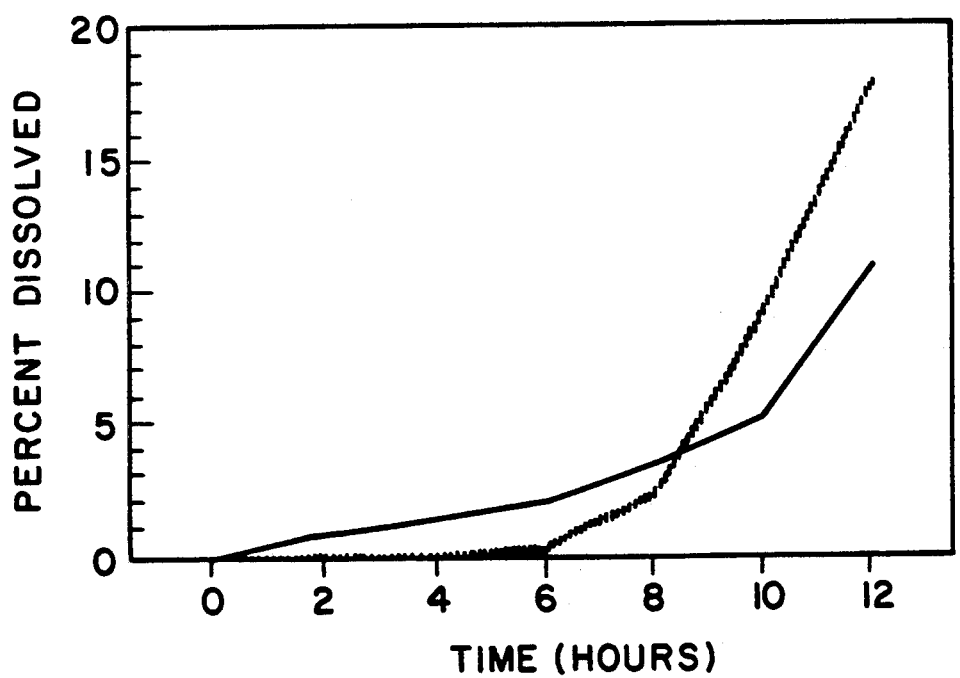
FIG. 20 is a graphical representation of the dissolution curve of the bilayered tablet of Example 25.

A representative tablet is then subjected to dissolution testing for the determination of the release of the tartrazine from one of the layers. A second representative tablet is subjected to dissolution testing to determine the release rate of Sulfan blue from the other layer. The results are graphically depicted in FIG. 20.

EXAMPLES 26-28

In Examples 26-28, the effect of including a hydrophobic material in the tablet core as a release modifying agent is examined.

In Example 26, a tablet core including 30 percent chlorphemiramine maleate, 69.5 percent Fast Flo ® lactose, and 0.5 percent magnesium stearate is compressed into the near-hemispherical shape of Example 12, and has a core weight of 350 mg, and a diameter of 10 mm. The tablet is coated with Surelease ® such that the coating comprises 15% by weight of the coated tablet. A 3.2 mm orifice is centrally made in the shallow convex face.

Example 27 is prepared in similar fashion as Example 26, except that the tablet core includes 30 percent chlorpheniramine maleate, 64.5 percent Fast Flo ® lactose, 5 percent hydrogenated vegetable oil, and 0.5 percent magnesium stearate.

Example 28 is also prepared in similar fashion as Example 26, except that the tablet core includes 30 percent chlorpheniramine maleate, 39.5 percent Fast Flo ® lactose, 30 percent hydrogenated vegetable oil, and 0.5 percent magnesium stearate.

Figure 21:
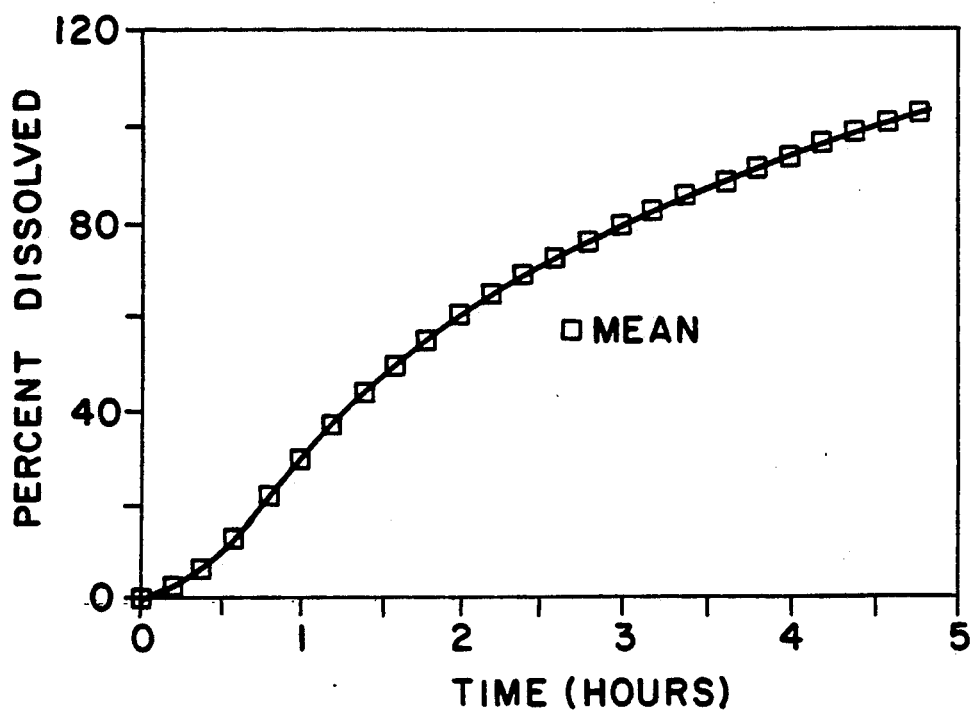
FIGS. 21–23 are graphical representations of the dissolution curves of the near-hemispherical tablets of Examples 26–28.
Figure 22:
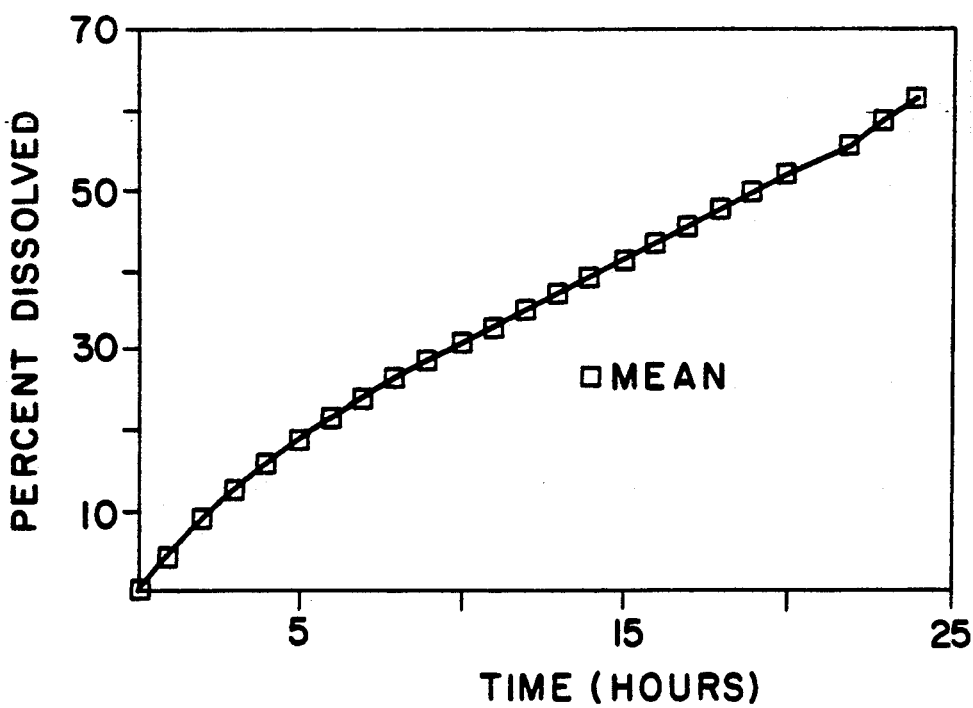
Figure 23:
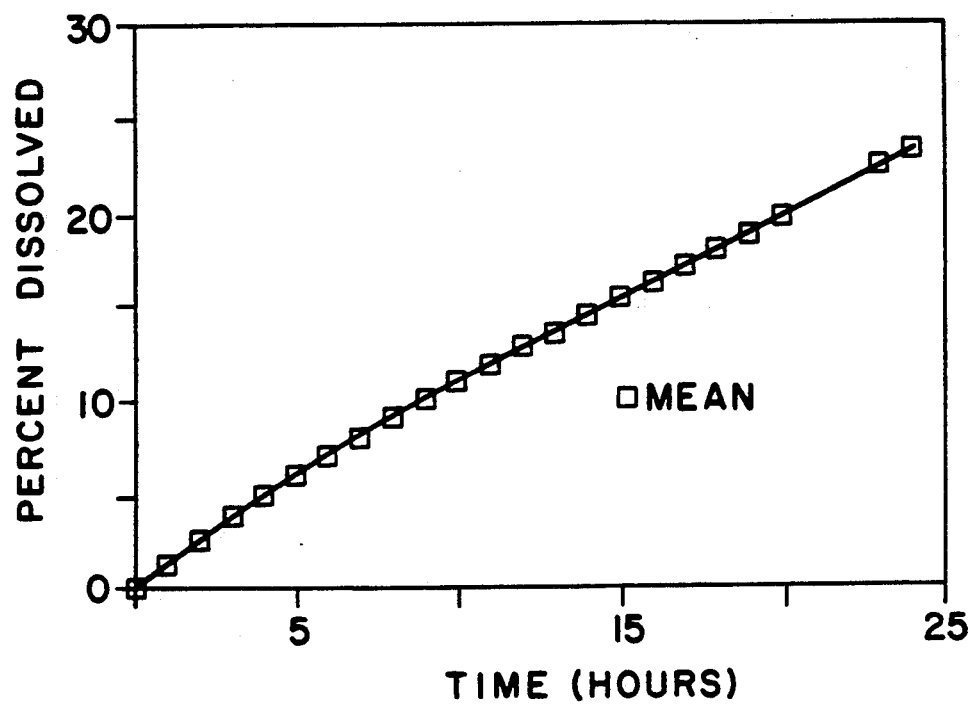

Representative tablets prepared according to each of Examples 26-28 are then subjected to dissolution testing. The results are graphically presented in FIGS. 21-23, respectively. The $T^{50}$ of Example 26 (no release modifying agent included) is 1.5 hours. In contrast, the $T^{50}$'s of Example 27 (5 percent hydrogenated vegetable oil) and Example 28 (30 percent hydrogenated vegetable oil) are 17 hours and 40 hours, respectively.

The examples provided above are not meant to be exclusive. Many other variations of the present invention would be obvious to those skilled in the art, and are contemplated to be within the scope of the appended claims.

I claim:

1. A device for controlled release of an active agent, comprising a core comprising an active agent and a release modifying agent; and an outer coating covering said core, the thickness of said coating being adapted such that it is substantially impermeable to the entrance of an environmental fluid present in an environment of use and substantially impermeable to the exit of said active agent during a dispensing period, said coating including an orifice extending substantially completely through said coating but not penetrating said core and communicating from said environment of use to said core for allowing the release of said active agent into said environment of use, said orifice having an area from about 10 to about 60 percent of the face area of said device, the rate limiting step for the release of said active agent substantially being the exit of said active agent through said orifice via one or more of dissolution, diffusion or erosion of said active agent in solution or suspension, said release modifying agent enhancing or hindering the release of said active agent depending upon the solubility and/or effective solubility of said active agent in said environment of use.

2. The device of claim 1, wherein said coating is selected from the group consisting of ethyl cellulose, acrylate polymers, polyamides, polymethacrylates, waxes, polyanhydrides, polyglycolides, polylactides, polybutyrates, polyvalerates, polycaprolactones, natural oils, polydimethylsiloxane, cross-linked or uncross-linked sodium carboxymethyl cellulose, sodium carboxymethylcellulose starch, polyvinylpyrollidone, cellulose ethers, cellulose acetate phthallate, polyvinylalcohol phthallate, shellac, zein, hydroxypropylmethyl cellulose phthallate, one or more of the above, and the like.

3. The device of claim 1, wherein said active agent is a drug.

4. The device of claim 3, wherein said device is a tablet and said environment of use is the gastrointestinal tract.

5. The device of claim 1, further comprising an adhesive coat between said core and said outer coating for improving adhesion of said outer coating to said core.

6. The device of claim 5, wherein said adhesive coat comprises shellac or polyvinyl acetate phthallate.

7. The device of claim 1 which is a biconvex tablet.

8. The device of claim 1, which has a first face which is deep convex and a second face which is substantially flat, shallow convex or shallow concave, said orifice being located on said second face.

9. The device of claim 1, wherein said core further comprises one or more excipients.

10. The device of claim 9, wherein said release modifying agent is selected from the group consisting of osmagents, effervescent bases, swelling agents, and soluble polymers.

11. The device of claim 1, wherein core comprises a first layer including a first active agent and a second layer including a second active agent, said device including a first orifice for releasing said first active agent and a second orifice for releasing said second active agent.

12. The device of claim 1, wherein said coating comprises ethyl cellulose.

13. The device of claim 1, wherein said coating comprises from about 90 to about 96.5 percent hydrogenated vegetable oil, from about 3 to about 5 percent polyvinylpyrollidone, and from about 0.5 to about 5 percent magnesium stearate.

14. The device of claim 1, wherein said orifice has a diameter corresponding to about 30 percent of the diameter of said device.

15. A controlled release tablet for oral administration, comprising
a core including an active agent and a release modifying agent,
an outer coating covering said core which is substantially impermeable to the entrance of gastrointestinal fluid and substantially impermeable to the release of said active agent during a predetermined dosing interval, said outer layer including an orifice for the release of said active agent during said dosing interval, said orifice extending substantially completely through said coating but not penetrating said core, the rate limiting step for the release of said active agent substantially being the exit of said active agent through said orifice via one or more of dissolution, diffusion or erosion of said active agent in solution or suspension, said release modifying agent enhancing or hindering the release of said active agent depending upon the solubility and/or effective solubility of said active agent in gastrointestinal fluid.

16. The tablet of claim 15, wherein said core is biconvex and said orifice is centrally located on a convex face of said tablet.

17. The tablet of claim 15, which has a first face which is deep convex and a second face which is substantially flat, shallow convex or shallow concave, said orifice being located on said second face.

18. The tablet of claim 15, wherein said coating is selected from the group consisting of ethyl cellulose, acrylate polymers, polyamides, polymethacrylates, biodegradable polymers, waxes, polyanhydrides, polyglycolides, polylactides, polybutyrates, polyvalerates, polycaprolactones, natural oils, polydimethylsiloxane, cross-linked or uncross-linked sodium carboxymethyl cellulose, sodium carboxymethylcellulose starch, polyvinylpyrollidone, cellulose ethers, cellulose acetate phthallate, polyvinylalcohol phthallate, shellac, zein, hydroxypropylmethyl cellulose phthallate, one or more of the above, and the like.

19. The table of claim 15, wherein said core further comprises one or more excipients.

20. The tablet of claim 19, wherein said release modifying agent is selected from the group consisting of osmagents, effervescent bases, swelling agents, and soluble polymers.

21. The tablet of claim 15, wherein said coating comprises ethyl cellulose.

22. The tablet of claim 15, wherein said coating comprises from about 90 to about 96.5 percent hydrogenated vegetable oil, from about 3 to about 5 percent polyvinylpyrollidone, and from about 0.5 to about 5 percent magnesium stearate.

23. The tablet of claim 18, wherein said tablet further comprises an adhesive coat between said core and said outer coating for improving adhesion of said outer coating to said core.

24. The tablet of claim 15, wherein said active agent has a aqueous solubility of about one part active to from about 1 part to about 1000 parts water.

25. The tablet of claim 15, wherein said orifice has a diameter corresponding to about 30 percent of the diameter of said tablet.

26. The device of claim 9, wherein said release modifying agent is selected from the group consisting of surfactants, hydrophobic materials, insoluble polymers, and ion exchange resins.

27. The table of claim 19, wherein said release modifying agent is selected from the group consisting of surfactants, hydrophobic materials, insoluble polymers, and ion exchange resins.

* * * * *